United States Patent [19]

Han

[11] Patent Number: 5,204,090
[45] Date of Patent: Apr. 20, 1993

[54] WATERPROOF HIGH-SPF SUNSCREEN COMPOSITIONS

[75] Inventor: Sie-Ta R. Han, Williamsville, N.Y.

[73] Assignee: Bristol Myers Squibb, New York, N.Y.

[21] Appl. No.: 707,473

[22] Filed: May 30, 1991

[51] Int. Cl.$^5$ .......................... A61K 7/42; A61K 7/44; A61K 7/48; A61K 9/12

[52] U.S. Cl. ................ 424/59; 424/DIG. 10; 424/47; 424/60; 424/63; 514/844; 514/847; 514/873; 514/944; 514/968

[58] Field of Search .................... 424/59, 60

[56] References Cited

U.S. PATENT DOCUMENTS

| | | | |
|---|---|---|---|
| 3,403,207 | 9/1968 | Kreps et al. | 424/60 |
| 3,485,915 | 12/1969 | Gerstein et al. | 424/60 |
| 4,193,989 | 3/1980 | Teng et al. | 424/60 |
| 4,254,102 | 3/1981 | Kaplan et al. | 424/59 |
| 4,293,544 | 10/1981 | Elmi | 424/60 |
| 4,671,955 | 6/1987 | Palinczar | 424/47 |
| 5,035,890 | 7/1991 | Braun | 424/59 |
| 5,036,108 | 7/1991 | Asahi et al. | 424/59 |
| 5,037,640 | 8/1991 | Schultz et al. | 424/59 |

OTHER PUBLICATIONS

Arlamol (R) E, ICI Americas, Inc., (1977), 10 pages.

*Primary Examiner*—Dale R. Ore
*Attorney, Agent, or Firm*—M. S. Simon

[57] ABSTRACT

Sunscreen compositions which are waterproof and have high-SPF values comprise a water insoluble film-forming polymer, a polyoxypropylene ether of straight or branched chain alcohol (the emollient/solvent) and a sunscreen component containing at least one UVB type sunscreen and/or at least one UVA type sunscreen in a topical vehicle, preferably in the form of an alcoholic gel. In particular, the combination of a polyoxyalkylene ether of a straight or branched chain alcohol, a carboxylated acrylic copolymer and a sunscreen agent yields waterproof, high-SPF compositions.

15 Claims, No Drawings

WATERPROOF HIGH-SPF SUNSCREEN COMPOSITIONS

FIELD OF THE INVENTION

This invention relates to waterproof, high-SPF sunscreen compositions comprising a film-forming polymer, an emollient/solvent system and sunscreen agent(s) in a vehicle suitable for topical administration. More particularly, this invention relates to the combination of a polyoxypropylene ether of straight or branched chain alcohol, a carboxylated acrylic copolymer and a sunscreen component in waterproof, high-SPF sunscreen products.

BACKGROUND OF THE INVENTION

Commercially available sunscreen products have been well known for decades to provide protection for the human skin against erythema-causing radiation. Products with different sun protection factor (SPF) values are available, thus allowing consumers to choose the amount of protection desired. SPF values range from about 1 upward, with higher values indicating higher degrees of sun protection. SPF values of 2–4 indicate minimal sun protection, 4–6 indicate moderate sun protection, 8–15 indicate maximal sun protection, and above 15 indicate ultra sun protection.

One important consideration when choosing a sunscreen is whether it resists coming off in water. "Water resistant" formulations can undergo about 40 minutes in water without significant SPF loss, whereas "waterproof" formulations can undergo 80 minutes in water without significant SPF loss.

"Waterproof" formulations are especially desirable because they eliminate the need for reapplication after swimming, bathing or excessive perspiration.

Other considerations can also be important when choosing a sunscreen product. For example, certain individuals are allergic to sunscreen compositions that contain p-aminobenzoic acid (PABA) or derivatives thereof, which are especially prevalent in higher SPF formulations. Furthermore, certain PABA derivatives cause stains which may be quite problematic and irritating.

Thus, it would be desirable to formulate waterproof sunscreen compositions which contain little or no PABA or PABA derivatives.

Certain UVA sunscreen agents, such as 2-hydroxy-4-methoxybenzophenone, commonly referred to as benzophenone-3 or oxybenzone, are often used in conjunction with UVB type sunscreen agents to effect a broader spectrum of sunscreen protection.

Benzophenone-3 absorbs ultraviolet rays in the higher UVA range of 3200–4000 Angstrom wavelengths, whereas UVB sunscreen agents, such as PABA, absorb ultraviolet rays in the more harmful erythemogenic and burning 2800–3200 Angstrom wavelength range.

Benzophenone-3 is often difficult to solubilize and maintain in solution, especially in the presence of water. It is more soluble in certain PABA esters, such as octyl dimethyl PABA, than it is in water and in alcohol. Higher concentrations of benzophenone-3 (up to about 6% by weight) are desirable in the formulation of sunscreens having higher SPF values. Heretofore, however, it has been difficult to achieve stable compositions containing benzophenone-3 at concentrations greater than about 3%. In fact, some products having higher concentrations maintain the benzophenone-3 in suspension rather than in solution.

A second problem confronted when formulating waterproof sunscreens is providing acceptable consistency, skin-feel and stability to the product. Those factors, which are important to achieving consistent distribution on the skin, even sun protection, consumer acceptance and commercial viability, are largely functions of the vehicle which carries the sunscreen agents.

For the above reasons, it would clearly be desirable to formulate a topical vehicle which is capable of providing acceptable consistency, skin feel and stability, and is also capable of solubilizing higher concentrations of benzophenone-3 and/or other sunscreen agents, and, thereby, achieve both waterproof character and high-SPF values.

SUMMARY OF THE INVENTION

The present invention provides a waterproof high-SPF sunscreen product comprising at least one water insoluble film-forming polymer, at least one polyoxyalkylene alcohol ether emollient/solvent, and a sunscreen component containing at least one UVB sunscreen and/or at least one UVA sunscreen. Optionally, at least one volatile alcohol carrier, a water soluble polymer and a thickening agent are used.

The term "high-SPF", as used herein, means a sun protection factor that offers at least maximal sun protection. The term includes SPF values of about 8 and greater.

In preferred embodiments, the present invention provides waterproof, high-SPF sunscreen compositions comprising:

(a) about 0.1 to about 90 weight percent of at least one water insoluble emollient selected from polyoxyalkylene ethers of straight or branched chain alcohols;

(b) about 0.01 to about 20 weight percent of at least one water insoluble film-forming carboxylated acrylic copolymer, that is preferably unneutralized;

(c) about 1 to about 30 weight percent of a sunscreen component containing at least one UVB sunscreen and/or at least one UVA sunscreen.

The present invention may optionally employ:

(d) about 0 to about 90 weight percent of at least one volatile liquid carrier selected from alcohols and volatile silicones;

(e) about 0 to about 15 weight percent of at least one water soluble/dispersible polymer and thickening agent, selected preferably from cellulose derivatives;

(f) about 0 to about 80 weight percent of water insoluble emollients, such as fatty acids; fatty alcohols; esters; ethers; oils; waxes and silicones;

(g) about 0 to about 80 weight percent of water soluble emollients, such as alcohols; alkoxylated alcohols; polyols and carbohydrates;

(h) about 0 to about 80 weight percent of water;

(i) about 0 to about 20 weight percent of viscosity increasing agents, such as natural gums and polymers; modified natural gums and polymers and synthetic polymers;

(j) about 0 to about 15 weight percent of emulsifiers; and (k) about 0 to about 85 weight percent of one or more insect repellent(s).

DETAILED DESCRIPTION OF THE INVENTION

The invention is concerned with waterproof sunscreen formulations and methods of protecting human skin from the effects of harmful ultraviolet radiation, e.g., erythema and burning, using effective amounts of same.

The sunscreen compositions preferably comprise a carboxylated acrylic copolymer, a polyoxypropylene ether of a straight or branched chain alcohol and sunscreen agent. Each of the ingredients is discussed below in greater detail.

Unless otherwise indicated, all percentages recited herein are weight percentages, based upon total composition weight.

All disclosures referred to herein are hereby incorporated by reference.

Carboxylated Acrylic Copolymers

Water insoluble carboxylated acrylic copolymers including those sold by National Starch and Chemical Corporation under the tradenames "Dermacryl", "Amphomer" and "Versacryl" (octylacrylamide/acrylates copolymer (CFTA), are known to be useful in this invention. It is known that these polymers become water dispersible/soluble via neutralization of their carboxyl groups with an alkaline material.

It has now been found that a solid copolymer "Dermacryl-79", which has been assigned the CTFA name copolymer provides satisfactory waterproof properties and higher SPF values when combined with an emollient containing a polyoxypropylene ether of straight or branched chain alcohol, an alcohol and one or more sunscreen agent(s).

In addition "Amphomer", or "octylacrylamide/acrylate/butylaminoethyl methacrylate copolymer", a polymer formed from octylacrylamide, t-butylaminoethyl methacrylate and two or more monomers consisting of acrylic acid, methacrylic acid or any of their simple esters, may be employed.

It is preferred that the water insoluble carboxylated acrylic copolymer used not be neutralized. Thus, preferred acrylic copolymers are those whose carboxyl groups have not been neutralized with amines or other alkaline material(s).

Generally, from about 0.01 to about 20 weight percent of carboxylated acrylic copolymer will be present in the sunscreen compositions of this invention. The range is preferably from about 1% to about 10%, with about 2% to about 8% being highly preferred.

Emollient/Solvent System

The emollient/solvent system of the invention basically comprises a polyoxypropylene ether of a straight or branched chain fatty alcohol or a polyoxypropylene/polyoxyethylene ether of a straight or branched chain alcohol having structure I:

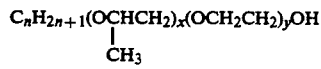

$$C_nH_{2n+1}(OCHCH_2)_x(OCH_2CH_2)_yOH$$
$$\phantom{C_nH_{2n+1}(O}|$$
$$\phantom{C_nH_{2n+1}(OCH}CH_3$$

wherein n is from about 2 to about 60, preferably about 12 to about 19, x is from about 2 to about 60, preferably about 5 to about 35, and y is from about 0 to about 50, preferably about 0 to about 30.

One preferred water insoluble emollient/solvent ingredient includes the polyoxypropylene 15 (PPG-15) stearyl ether sold by ICI Americas Inc. under the tradename "Arlamol E". It is known to be an excellent solvent for sunscreens and many cosmetics.

It has been found that "Arlamol E", which is a colorless to light yellow oily liquid, can provide satisfactory results in maintaining benzophenone-3 in solution. More particularly, when "Arlamol E" is combined with "Dermacryl-79" and sunscreen agent(s), waterproof, high-SPF compositions are obtained.

Useful polyalkylene ethers include the fatty alcohol polyoxypropylene ethers sold as "Hexconal SP15" (Heterene Chem. Co., Paterson, N.J.), "Prostearyl 15" and polypropylene glycol (15) stearyl ether.

Generally, from about 0.1 to about 90 weight percent of at least one polyalkylene oxide ether of a $C_{2-60}$ straight or branched chain alcohol will be present in the sunscreen products of this invention. The preferred range is about 1% to about 60%, with about 2% to about 30% being highly preferred.

Sunscreen Agents

The term "sunscreen agent" as used herein includes commonly used ultraviolet ray-blocking compounds such as ethylhexyl p-methoxycinnamate, butyl methoxydibenzoylmethane, 2-hydroxy-4-methoxybenzophenone (benzophenone-3), octyl dimethyl p-aminobenzoic acid, digalloyl trioleate, 2,2-dihydroxy-4-methoxy benzophenone, ethyl 4-[bis(hydroxypropyl)]aminobenzoate, 2-ethylhexyl 2-cyano-3,3-diphenylacrylate (octocrylene), ethyl hexyl p-methoxy cinnamate, 2-ethylhexyl salicylate, glyceryl p-aminobenzoate, 3,3,5-trimethylcyclohexyl salicylate, menthyl anthranilate, p-dimethyl aminobenzoate, and 2-ethylhexyl p-dimethyl amino benzoate and the like. Mixtures of these compounds may also be used.

A more detailed discussion of sunscreen agents useful in this invention is provided by Roelandts et al., "A Survey of Ultraviolet Absorbers in Commercially Available Sun Products", *Int. J. Dermatol.*, Vol. 22, pp. 247-255 (May, 1983).

The amount of sunscreen component useful in the sunscreen compositions of the present invention is from about 1% to about 30%, with the exact percentage dependent upon the particular agent(s) chosen and SPF level desired.

Optional Components

The cellulosic portion of the compositions may use polymeric cellulosics and their derivatives, such as hydroxyethyl cellulose, hydroxymethyl cellulose and, preferably, hydroxypropyl cellulose. This component functions as a gelling agent and is present at concentrations of about 0% to about 2%.

Useful gellants also include carbopols and other conventional thickeners in suitable amounts.

In addition, the emollient/solvent system may contain from about 0 to about 90%, preferably about 10 to about 85 of a $C_{1-12}$, preferably a $C_{1-4}$, alcohol in which the unneutralized carboxylated copolymer component is soluble. Denatured ethyl alcohol used as a solvent and as a volatile liquid carrier, and termed "SD Alcohol 40" is highly preferred.

The compositions of the invention will generally contain suitable amounts of cosmetically and pharmaceutically acceptable additives, i.e., excipients and/or chemically active adjuvants.

Among such additives are colorants, thickeners, perfumes, fillers, diluents, carriers, plasticizers, stabilizers, gelling agents, surfactants, fixatives, supplemental screening agents, preservatives for screening agents, supplemental emollients/solvents and the like. Quantities of about 0.001 to about 99.99% of these additives can be used. Mixtures are operable.

Useful preservatives for screening agents include antioxidants, such as hydroquinone, citric acid, butylated hydroxytoluene, butylated hydroxyanisole and the like. Mixtures can be employed.

Supplemental emollients and solvents for use in the compositions of the invention include among others, propylene glycol, dipelargonate, myristyl lactate, lauryl lactate and decyl oleate. Mixtures may be used.

Use

The form in which the formulations of the invention are used can vary. Readily flowable liquids, such as sprays, i.e., both aerosol and non-aerosol, paints and dips are advantageous for ease of application. However, the water resistance of the sunscreen will be enhanced by formulating it for use as a paste, ointment, salve, gel or cream, which would dry relatively quickly to leave a water resistant or waterproof film on the skin.

While alcoholic systems are described in detail herein, aqueous emulsions and anhydrous systems are also contemplated.

"Effective amount(s)" may vary depending upon frequency of application and/or contact with moisture. The formulations are typically used by applying from 0.1 to 20 microliters per square centimeters of same for the skin of a subject and allowing it to dry. Reapplication can be made from one to several time per day, with the total number of daily applications being from about 1 to about 8 times.

EXAMPLES

Procedures

A. Mixing Procedures

In the examples, the following mixing procedures were employed:

Admix the ingredients in Part A, at a temperature of 25° C., in a stainless steel vessel, equipped with a stirrer until a homogeneous admixture is formed. Slowly admix the ingredient in Part C into Part A, until a homogeneous admixture is formed. Admix the ingredients of Part B in a separate stainless steel vessel until a homogeneous admixture is formed. Admix Part B to the admixture of Parts A and C until a homogeneous admixture is formed.

B. Determination of Waterproof SPF Values

The waterproof SPF values discussed herein were determined by the following procedure. It is based on the methodology for measuring waterproof SPF published by the FDA in the proposed monograph for OTC sunscreens (FDA Document #166).

Waterproof SPF testing was performed on healthy volunteer subjects having skin types I, II and III, which are defined as follows:

| Skin type | Sunburn and tanning history |
| --- | --- |
| I | Always burns easily; never tans |
| II | Always burns easily; tans minimally |
| III | Burns moderately; tans gradually |
| IV | Burns minimally; always tans well |
| V | Rarely burns; tans profusely |
| VI | Never burns; deeply pigmented. |

For each subject, the preliminary minimal erythema dose (MED) of ultraviolet (UV) radiation was determined by administering graded doses of UV, increasing by 25% for each exposure, to an unprotected skin site on the mid-back using a xenon arc solar simulator. The erythemal responses were evaluated 24 hours later.

The following grading scale was used for clinical measurements of erythema:

| | |
| --- | --- |
| 0 | No erythema |
| 1 | Minimally perceptible, but definite erythema, without well-defined borders |
| 2 | Erythema with well-defined borders |
| 3 | Intense erythema with edema. |

The lowest UV dose which produced an erythema grade of 1 or higher was defined as the preliminary MED.

Sunscreen formulations were then applied, in an amount of 2 microliters per square centimeter, uniformly on different skin sites of the mid-back and allowed to dry for 15 minutes. The subjects then completed four, 20-minute periods of simulated swimming in a whirlpool bath.

UV exposures were administered to sunscreen protected and unprotected sites using the same solar simulator. The exposures for the sunscreen-protected sites were multiples of the previously determined preliminary MED, increasing by 25% for each exposure. The erythemal response to each UV dose was evaluated 24 hours after administration to yield the final unprotected MED and the MED for the sunscreen protected site.

The waterproof SPF for each product were calculated as the ratio of the MED for sunscreen-protected skin to that for unprotected skin. That is, $$\text{Waterproof } SPF = \frac{MED \text{ for protected skin}}{MED \text{ for unprotected skin}}.$$

| Ingredient | Weight percent |
| --- | --- |
| Example 1: Sunscreen gel SPF 3 | |
| Part A | |
| SD Alcohol 40* | 56.5 |
| PVP/Hexadecene copolymer* | 4.0 |
| Part B | |
| Octyl Methoxycinnamate | 7.5 |
| Benzophenone-3 | 6.0 |
| Octyl Salicylate | 5.0 |
| Diisopropyl adipate | 20.0 |
| Part C | |
| Hydroxypropyl cellulose | 1.0 |
| Example 2: Waterproof Sunscreen gel SPF 17 | |
| Part A | |
| SD Alcohol 40 | 57.5 |
| Acrylates/t-Octylpropenamide copolymer | 3.0 |
| Part B | |
| Octyl Methoxycinnamate | 7.5 |
| Benzophenone-3 | 6.0 |
| Octyl Salicylate | 5.0 |
| Diisopropyl adipate | 20.0 |
| Part C | |

| Ingredient | Weight percent |
| --- | --- |
| Hydroxypropyl cellulose | 1.0 |

*SD Alcohol 40 is denatured ethyl alcohol
**Ganex V-516 (GAF Corporation)

The difference between Example 1 and Example 2 is in the different type of polymer used in the formulation. The waterproof SPF values measured were 3 and 17 respectively. The results clearly indicate that "Dermacryl-79" offers waterproofing properties for sunscreen products.

However, when "Dermacryl-79" and "Arlamol E" were combined in sunscreen formulations, unexpected waterproof high-SPF values were obtained. The following two examples demonstrate such formulations. The sunscreen formulations of Examples 3 and 4 are substantially clear gels at ambient temperature and offer high sun protection factor (SPF) as well as waterproof properties when applied topically.

| Ingredient | Weight percent |
| --- | --- |
| Example 3: Waterproof sunscreen gel SPF 30 | |
| Part A | |
| SD Alcohol 40 | 68.8 |
| Acrylates/t-Octylpropenamide Copolymer | 2.0 |
| Part B | |
| Octyl Methoxycinnamate | 7.5 |
| Benzophenone-3 | 6.0 |
| Octyl Salicylate | 5.0 |
| PPG-15 Stearyl Ether | 10.0 |
| Part C | |
| Hydroxypropyl cellulose | 0.7 |
| Example 4: Waterproof sunscreen gel SPF 27 | |
| Part A | |
| SD Alcohol 40 | 71.3 |
| Acrylates/t-Octylpropenamide Copolymer | 2.0 |
| Part B | |
| Octyl Methoxycinnamate | 5.0 |
| Benzophenone-3 | 6.0 |
| Octyl Salicylate | 5.0 |
| PPG-15 Stearyl Ether | 10.0 |
| Part C | |
| Hydroxypropyl cellulose | 0.7 |

Using the procedure described above, the waterproof SPF values of Example 3 and Example 4 were measured to be 30 and 27 respectively.

The following are other examples which, by following the general procedure of Example 1, produce high-SPF waterproof sunscreen products.

| Ingredient | Weight percent |
| --- | --- |
| Example 5: Waterproof sunscreen gel | |
| Part A | |
| SD Alcohol 40 | 68.3 |
| Acrylates/t-Octylpropenamide Copolymer | 2.0 |
| Part B | |
| Octyl Dimethyl PABA | 8.0 |
| Benzophenone-3 | 6.0 |
| Octyl Salicylate | 5.0 |
| PPG-15 Stearyl Ether | 10.0 |
| Part C | |
| Hydroxypropyl cellulose | 0.7 |
| Example 6: Insect repelling waterproof sunscreen gel | |
| Part A | |
| SD Alcohol 40 | 53.5 |
| Acrylates/t-Octylpropenamide Copolymer | 2.0 |
| Part B | |
| Octyl Methoxycinnamate | 7.5 |
| Benzophenone-3 | 6.0 |
| Octyl Salicylate | 5.0 |
| PPG-15 Stearyl Ether | 10.0 |
| DEET | 15.0 |
| Part C | |
| Hydroxypropyl cellulose | 1.0 |
| Example 7: Waterproof sunscreen gel | |
| Part A | |
| SD Alcohol 40 | 54.8 |
| Acrylates/t-Octylpropenamide Copolymer | 3.0 |
| Part B | |
| Octyl Dimethyl PABA | 8.0 |
| Octyl Methoxycinnamate | 7.5 |
| Benzophenone-3 | 6.0 |
| Octyl Salicylate | 5.0 |
| PPG-15 Stearyl Ether | 10.0 |
| Diisopropyl adipate | 5.0 |
| Part C | |
| Hydroxypropyl cellulose | 0.7 |

Reasonable variations, such as those which would occur to a skilled artisan, can be made herein without departing from the scope of the invention.

What is claimed is:

1. A waterproof high-SPF Sunscreen composition comprising:
   (a) from about 1 weight % to about 10 weight % based on the total weight of the composition, of a water insoluble carboxylated acrylic copolymer selected from the group consisting of acrylate/t-octylpropenamide, octylacrylamide/acrylate/butylaminoethyl methacrylate copolymer, sand octylacrylamide/acrylates copolymer;
   (b) from about 1 weight % to about 60 weight % of polyoxypropylene (15) stearyl ether;
   (c) from about 1 weight % to about 30 weight % of a sunscreen component containing at least one UVB sunscreen and/or at least one UVA sunscreen.

2. The composition of claim 1 wherein the copolymer comprises a acrylate/t-octylpropenamide copolymer.

3. The composition of claim 2 comprising: about 2% to about 3% of acrylate/t-octylpropenamide copolymer and about 10% of polyoxypropylene (15) stearyl ether.

4. The composition of claim 3 comprising about 6% of benzophenone-3 and about 5% of octyl salicylate.

5. The composition of claim 4 comprising from about 5.0% to about 7.5% of octyl methoxycinnamate.

6. The composition of claim 5 comprising about 8% of octyl dimethyl p-aminobenzoic acid.

7. The composition of claim 4 comprising from about 8% of octyl dimethyl p-aminobenzoic acid 8. The composition of claim 4 comprising from about 5% to about 8% of octyl dimethyl p-aminobenzoic acid.

9. The composition of claim 4 comprising from about 3% to about 7.5% of octyl methoxycinnamate.

10. The composition of claim 2 comprising:
   (a) from about 2% to about 8% of acrylate/t-octylpropenamide copolymer;
   (b) from about 2% to about 30% of polyoxypropylene (15) stearyl ether;
   (c) from 0% to about 10% of p-aminobenzoic acid or derivative thereof;
   (d) from 0% to about 7.5% of octyl methoxycinnamate;
   (e) from 0% to about 5% of octyl salicylate;
   (f) from 0% to about 6% of benzophenone-3; and (g) from about 0 to about 2.0% hydroxypropyl-cellulose.

11. The composition of claim 10 said composition further containing from about 0 to about 90 weight % of a $C_{1-12}$ alcohol in which the copolymer is soluble.

12. The composition of claim 10 wherein the composition further contains water and an emulsifying agent, and is an aqueous emulsion.

13. The composition of claim 10 wherein the composition is anhydrous.

14. A method of protecting human skin from the harmful effects of ultraviolet light comprising the step of topically applying to the skin an amount which is effective to protect the skin from said harmful effects of the composition of claim 1.

15. A method of protecting human skin from the harmful effects of ultraviolet light comprising the step of topically applying to the skin an amount which is effective to protect the skin from said harmful effects of the composition of claim 10.

* * * * *